United States Patent [19]

Sasaki

[11] Patent Number: 4,553,964
[45] Date of Patent: Nov. 19, 1985

[54] INFUSION APPARATUS

[75] Inventor: Hideki Sasaki, Hiroshima, Japan

[73] Assignee: Japan Medical Supply Co., Ltd., Hiroshima, Japan

[21] Appl. No.: 584,119

[22] Filed: Feb. 27, 1984

[30] Foreign Application Priority Data

Mar. 14, 1983 [JP] Japan .................... 58-35532[U]

[51] Int. Cl.⁴ .................................................. A61M 5/14
[52] U.S. Cl. .................................. 604/248; 604/251; 604/410
[58] Field of Search .............. 604/122, 248, 249, 251, 604/256, 405, 410

[56] References Cited

U.S. PATENT DOCUMENTS 3,001,397  9/1961  Leonard .............................. 604/251

*Primary Examiner*—Melvyn J. Andrews
*Attorney, Agent, or Firm*—Kramer & Brufsky

[57] ABSTRACT

An infusion apparatus is provided which can give an infusion with high precision and which allows each changing of the infusion capacity. The apparatus includes a first burette and a second burette connected in series. The burettes communicate with each other through a connector which can be selectively opened or closed by directional control valve means.

12 Claims, 12 Drawing Figures

INFUSION APPARATUS

BACKGROUND OF THE INVENTION

This invention relates to an infusion apparatus for quantitatively dosing patients with a medicinal solution such as Ringer's solution, glucose solution, an antibiotic or the like, and is particularly concerned with an infusion apparatus wherein a plurality of burettes adapted to contain at least one medicinal solution are coupled to communicate with each other in series through a communicating passage, and directional control valve means capable of selectively opening and closing the communicating passage is provided within the communicating passage.

A graduated burette is well known as an infusion burette. The conventional burette is generally a cylinder with a capacity of 100 ml or 200 ml, normally graduated in 1 ml increments. Dosage control is extremely important in infusion, and, depending on the circumstances, the capacity of the burette in service may need to be changed. If the burette in service has to be changed to a burette having another capacity, it can be quite painful for the patient and also troublesome to the person making the change. Further, the conventional burette does not fulfill the requirement for high precision infusion. Particularly in dosing antibiotics, an infusion of high precision is required. Thus, there is a real need for a burette capable of meeting these requirements—which need has gone unanswered prior to the advent of the present invention.

SUMMARY OF THE INVENTION

Accordingly, it is an object of the present invention to provide an infusion apparatus capable of infusing with high precision and which permits easy change of infusion capacity with essentially no discomfort to the patient.

According to the present invention, an infusion apparatus is provided comprising a first burette, a second burette and a connector, said burettes communicating in series with each other through said connector—said connector having a first passageway therethrough for establishing communication between said first and second burettes, said connector having a second passageway therein communicating with and adapted to introduce air into said second burette, and directional control valve means positioned across both said first and second passageways and adapted to close said first passageway when said second passageway is opened and to open said first passageway when said second passageway is closed.

In a preferred embodiment, the first burette and the second burette are different from each other in diameter and capacity, and each burette is graduated differently in unit quantity per graduation; therefore, the burette smaller in unit quantity per graduation is used when a small quanity of solution is to be precisely infused, and the one of larger capacity is used when infusing more solution. Thus the apparatus of this invention is capable of easily performing a variety of infusion operations.

Furthermore, in accordance with this invention, directional control valve means are provided by a segmented spool plug valve and, in another embodiment, by a three-way plug cock.

BRIEF DESCRIPTION OF THE DRAWINGS

The present invention will be better understood by reference to the accompanying drawings wherein.

DESCRIPTION OF THE PREFERRED EMBODIMENT

Figure 1:
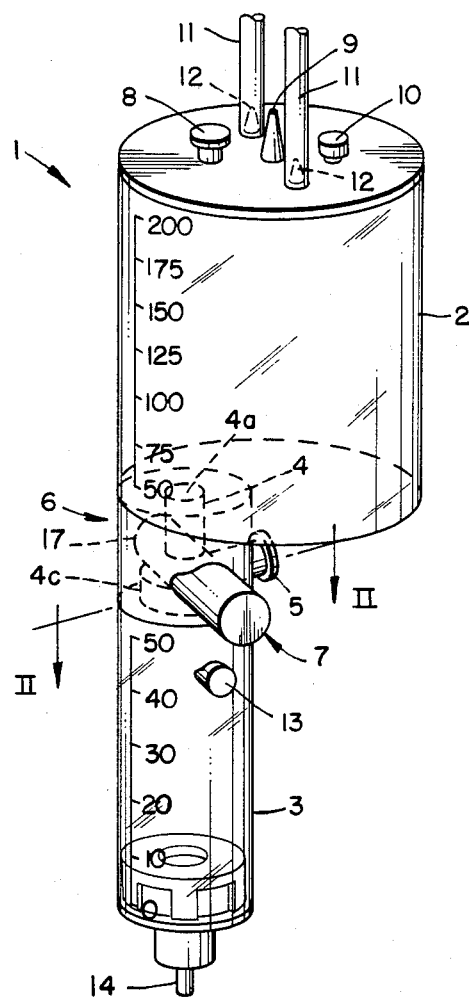
FIG. 1 is a perspective view of an infusion apparatus of the present invention.

FIG. 1 illustrates one embodiment of an infusion apparatus 1 of this invention. The infusion apparatus 1 comprises an upper burette 2, a lower microburrette 3, a connector 6 is provided with a communicating passageway 4 for coupling the upper burette 2 and the lower microburette 3 to communicate with each other and an air introducing passageway 5 which can be provided with a bacteria filter and which is capable of communicating with the lower microburette 3, and directional control valve means 7 capable of selectively opening and closing the communicating passageway 4 and the air introducing passageway 5.

An air introducing passageway 8 which can contain a bacteria filter, a principal medicinal solution introducing passageway 9 and an auxiliary medicinal solution injection passageway 10 are also provided in a cover of the upper burette 2, and further a pair of projections 12 for installing supporting lines 11 used to support the infusion apparatus 1 are formed thereon.

An auxiliary medicinal solution injection port 13 is also provided on the lower microburette 3, and an infusion outlet passageway 14 is formed on its lower end.

The upper burette 2, in one embodiment, has a capacity of 150 ml and is graduated in 1 ml units on its outside wall surface. On the other hand, the lower microburette 3 which has a different diameter from the upper burette 2 has a capacity of 50 ml and is graduated in 0.5 ml units on its outside wall surface.

The connector 6 is integral with the lower end of the upper burette 2, and both the lower end of the connector and the upper end of the lower microburette 3 are coupled in an airtight manner. It is considered preferable that the upper burette 2, coupled as above, the connector 6 and the lower microburette 3 be formed of a transparent material such as plastic or the like so that a medicinal solution injected therein can be observed easily from outside.

Figure 2:
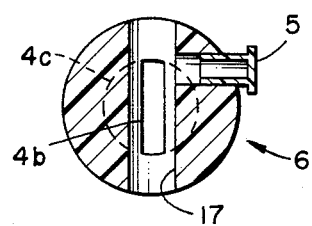
FIG. 2 is a sectional view taken on the line II—II of FIG. 1 and in which a valve is excluded for ease of visualization and description.
Figure 3:
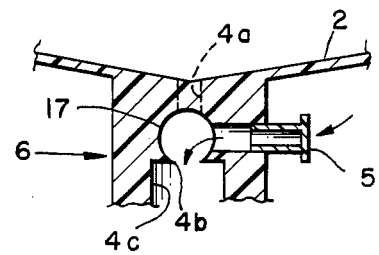
FIG. 3 is a longitudinal sectional view of a connector.
Figure 4:
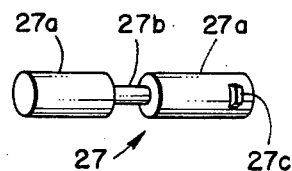
FIG. 4 is a perspective view of a segmented spool plug valve member.

With reference to FIGS. 1–3, the communicating passageway 4 is provided vertically at the center of the connector 6, and a circular aperture 17 is provided orthogonally to the communicating passageway 4 at the center thereof in a transverse section of the connector 6, the circular aperture 17 communicating with the air introducing passageway 5. The communicating passageway 4 is formed of a smaller diameter portion 4a, a circular aperture 17, a groove 4b and a larger diameter portion 4c. A segmented spool plug valve 27 (FIG. 4) provided with a larger diameter portion 27a, a smaller diameter portion 27b and a stopper 27c, is slidably fitted in the circular aperture 17.

Figure 5:
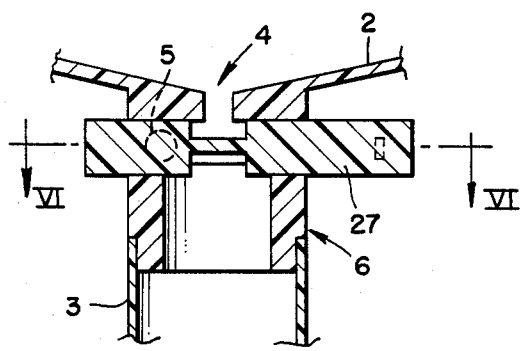
FIG. 5 is a longitudinal sectional view of a connector in the state where a communicating passage for a medicinal solution is open.
Figure 6:
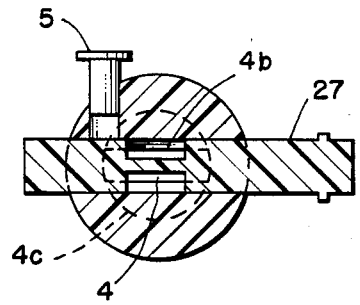
FIG. 6 is a sectional view taken on the line VI—VI of FIG. 5.

The position of the spool plug valve 27 when the infusion apparatus 1 of this embodiment is used for infusion of 200 ml is shown in FIG. 5 and FIG. 6. As is apparent from the drawings, the spool plug valve 27 opens the passageway 4 for a medicinal solution, closes the air introducing passageway 5 and interrupts the introduction of air into the lower microburette 3, thereby perferctly preventing leakage of the medicinal solution. In this state, the medicinal solution in the upper burette 2 flows through the communicating passageway 4 into the lower microburette 3.

Figure 7:
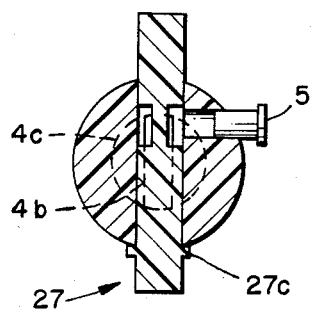
FIG. 7 is a transverse sectional view of the connector in the state where the air introducing passageway is open.
Figure 8:
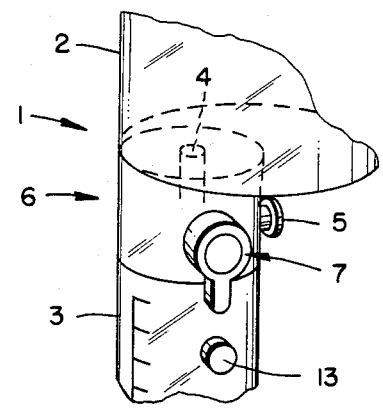
FIG. 8 is a perspective view of another example of the valve.

Next, by depressing and moving the spool plug valve 27 until it stops on the stopper 27c, the infusion apparatus 1 of this embodiment can be used for infusing a small quantity of medicinal solution. The position of the spool plug valve 27 in this case is shown in FIG. 7. As is apparent from the illustration, the spool plug valve 27 closes the passageway 4 for the medicinal solution and opens the air introducing passageway 5, allowing the air to flow from the air introducing passageway 5 into the lower microburette 3, and also interrupts the flow of the medicinal solution from the upper burette 2 into the lower microburette 3. Thus, the lower microburette 3 can be used independently as a microburette graduated in 0.5 ml units. The flow route of the air in this case is shown by an arrow in FIG. 3.

The larger diameter portion 27a of the spool plug valve 27 in the above embodiment is cylindrical and has no directional property in the circumferential direction; therefore, it functions as a directional control valve even when it is rotated at the time of opening and closing of the communicating passageway 4. Accordingly, it is not necessary to ensure the position of the valve in the circumferential direction when the state of the communicating passageway 4 is changed, which is very convenient.

Figure 9:
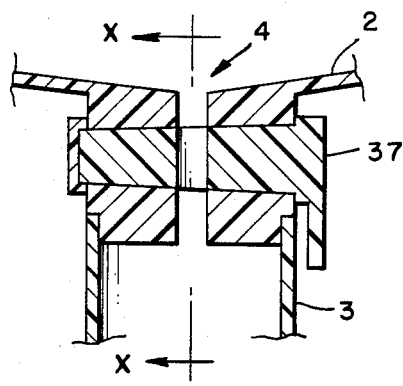
FIG. 9 is a longitudinal sectional view of the connector in the state where the communicating passageway for the medicinal solution is open.
Figure 10:
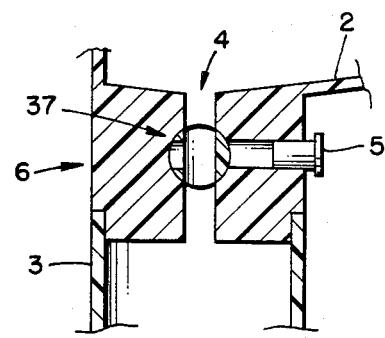
FIG. 10 is a sectional view taken on the line X—X of FIG. 9.
Figure 11:
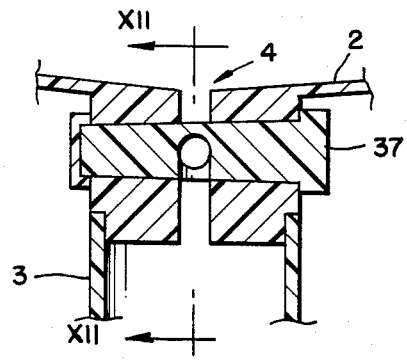
FIG. 11 is a longitudinal sectional view of the connector in the state where the air introducing passageway is open.
Figure 12:
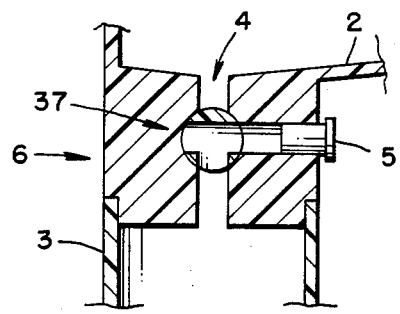
FIG. 12 is a sectional view taken on the line XII—XII of FIG. 11.

Another embodiment of the directional control valve mechanism 7 will be described with reference to FIGS. 8–12. In this embodiment, a three-way plug cock 37 is employed for the directional control valve instead of the spool plug valve described above. The position of the three-way plug cock 37 when the infusion apparatus 1 according to this embodiment is used for a large quantity infusion is shown in FIGS. 9 and 10. In this case, the three-way plug cock 37 opens the passageway 4 for the medicinal solution and closes the air introducing passageway 5. When the three-way plug cock 37 is then turned 90°, it becomes as illustrated in FIGS. 11 and 12, the passageway 4 for the medicinal solution is closed, and the air introducing passageway 5 is opened. Therefore, the infusion apparatus 1 is prepared for infusing small quantities of solution by the above operation of the three-way plug cock 37.

Also, instead of forming the connector 6 in one body with the upper burette 2, it can be formed in one body with the lower microburette 3, or formed separately and adapted to be fitted in an airtight fashion to the upper burette 2 and the lower microburette 3 during use.

Furthermore, for opening or closing the directional control valve means 7, a predetermined length of groove is provided axially of the spool plug valve 27, and the groove can be constituted so as to communicate with the air introducing passageway 5 according to the movement of the spool plug valve 27.

According to the above embodiment, a burette of 150 ml in capacity and a microburette of 50 ml in capacity are kept in communication with each other through a connector, and directional control valve means capable of selectively opening and closing a passageway for a medicinal solution and an air introducing passageway is provided on the connector, so that a large quantity infusion apparatus (200 ml in capacity) can be transformed to a (50 ml) small quantity infusion apparatus even during infusion, and further the transforming operation is quite simplified and easily facilitated without pain to the patient. The 0.5 ml graduations given on the 50 ml microburette may help ensure an infusing operation at a higher precision than with a conventional type of burette. Furthermore, a medicinal solution can be stored in the upper burette while the communicating passageway for the medicinal solution is interrupted and the lower microburette can be used independently, thereby cutting the loss of time between infusions.

As described in detail above, according to this invention, an infusion apparatus advantageous in practice can be provided such that an infusion capacity can easily be changed despite the apparatus being one unit, and further, a high precision infusion can be effected.

What is claimed is:

1. An infusion apparatus comprising a first upper burette, a second lower burette and a connector, said burettes communicating in series with each other through said connector, said connector having a first passageway therethrough for establishing communication between said first and second burettes, said connector having a second passageway therein communicating with and adapted to introduce air into said second burette, and directional control valve means positioned across both said first and second passageways and adapted to close said first passageway when said second passageway is opened and to open said first passageway when said second passageway is closed.

2. The infusion apparatus as defined in claim 1, wherein said first burette and second burette are cylinders different in diameter from each other.

3. The infusion apparatus as defined in claim 2, wherein said first burette and second burette are each graduated, and the unit quantity of the graduations is different on said first burette and on said second burett.

4. The infusion apparatus as defined in claim 1, wherein said directional control valve means is provided with a spool plug valve.

5. The infusion apparatus as defined in claim 1, wherein said directional control valve means is provided with a three-way plug cock.

6. The infusion apparatus as defined in claim 1, wherein said conenctor is formed in one body with said first burette.

7. The infusion apparatus as defined in claim 1, wherein said first burette contains an air-introducing passageway therein.

8. The infusion apparatus as defined in claim 1, wherein said first burette contains a passageway therein for introducing a medicinal solution thereto.

9. The infusion apparatus as defined in claim 8, wherein said first burette additionally contains a passageway therein for introducing an auxiliary medicinal solution thereto.

10. The infusion apparatus as defined in claim 1, wherein said first burette contains receiving means therein adapted to receive lines adapted to support the infusion apparatus.

11. The infusion apparatus as defined in claim 1, wherein said second burette contains a passageway therein for introducing an auxiliary medicinal solution thereto.

12. The infusion apparatus as defined in claim 1, wherein the second burette contains an infusion outlet passageway in the terminal portion thereof opposite that portion thereof in contact with the connector.

* * * * *